(12) United States Patent
Hsieh et al.

(10) Patent No.: US 7,440,602 B2
(45) Date of Patent: Oct. 21, 2008

(54) METHODS, APPARATUS, AND SOFTWARE TO COMPENSATE FOR FAILED OR DEGRADED COMPONENTS

(75) Inventors: Jiang Hsieh, Brookfield, WI (US); Charles Addison Bouman, West Lafayette, IN (US); Ken David Sauer, South Bend, IN (US); Jean-Baptiste Thibault, Milwaukee, WI (US)

(73) Assignees: General Electric Company, Schenectady, NY (US); Purdue Research Foundation, West Lafayette, IN (US); The University of Notre Dame du lac, Notre Dame, IN (US)

( * ) Notice: Subject to any disclaimer, the term of this patent is extended or adjusted under 35 U.S.C. 154(b) by 654 days.

(21) Appl. No.: 10/990,921

(22) Filed: Nov. 17, 2004

(65) Prior Publication Data

US 2006/0104536 A1  May 18, 2006

(51) Int. Cl.
*G06K 9/00* (2006.01)

(52) U.S. Cl. .......................... 382/128; 382/220; 378/21

(58) Field of Classification Search ................. 382/128, 382/129, 130, 131, 132, 133, 168, 181, 232, 382/254, 260, 274, 275, 276, 100, 203, 220; 378/15, 16, 4, 19, 20, 21
See application file for complete search history.

(56) References Cited

U.S. PATENT DOCUMENTS

| | | | |
|---|---|---|---|
| 6,173,032 B1 * | 1/2001 | Besson | 378/19 |
| 6,194,726 B1 | 2/2001 | Pi et al. | |
| 6,226,350 B1 | 5/2001 | Hsieh | |
| 6,233,308 B1 | 5/2001 | Hsieh | |
| 6,389,097 B1 | 5/2002 | Bulkes et al. | |
| 6,421,411 B1 * | 7/2002 | Hsieh | 378/4 |
| 6,490,335 B1 * | 12/2002 | Wang et al. | 378/15 |
| 6,529,576 B2 * | 3/2003 | Hsieh et al. | 378/15 |
| 7,116,749 B2 * | 10/2006 | Besson | 378/16 |
| 7,187,794 B2 * | 3/2007 | Liang et al. | 382/131 |

* cited by examiner

*Primary Examiner*—Seyed Azarian
(74) *Attorney, Agent, or Firm*—Armstrong Teasdale LLP

(57) ABSTRACT

A method for improving images of an imaging system including a plurality of detector cells includes assigning a quality factor for each detector cell.

20 Claims, 2 Drawing Sheets

METHODS, APPARATUS, AND SOFTWARE TO COMPENSATE FOR FAILED OR DEGRADED COMPONENTS

BACKGROUND OF THE INVENTION

This invention relates generally to methods, apparatus and software for image reconstruction and, more particularly, to the lessening of image degradation due to failed or degraded components.

With a continued pursuit of larger volume coverage in imaging modalities, the number of detector channels and Data Acquisition System (DAS) channels increase quickly. As a result, the probability of the detector channel, interconnections, and DAS failure or degradation increases. Although theoretically the replacement of a failed detector and DAS is possible, replacement of failed high channel number detectors and DAS can be expensive. In addition, clinical operation may be interrupted due to the CT system downtime. Therefore, when the number of detector channels on a system is large, it may not be economical to replace all the failed components. It is desirable to derive a scheme in which the failed or degraded detector or DAS will not produce image artifacts or significant degradation in image quality.

BRIEF DESCRIPTION OF THE INVENTION

In one aspect a method for improving images of an imaging system including a plurality of detector cells is provided. The method includes assigning a quality factor for each detector cell.

In another aspect, an imaging system includes a radiation source, a detector array including a plurality of cells positioned to receive radiation from the source, and a computer coupled to the detector array. The computer is configured to obtain from a memory a quality factor for each detector cell, and use the quality factors to reconstruct an image.

In yet another aspect, a computer readable medium encoded with a program is provided. The program is configured to instruct a computer to assign a quality factor for each of a plurality of detector cells.

DETAILED DESCRIPTION OF THE INVENTION

Figure 1:
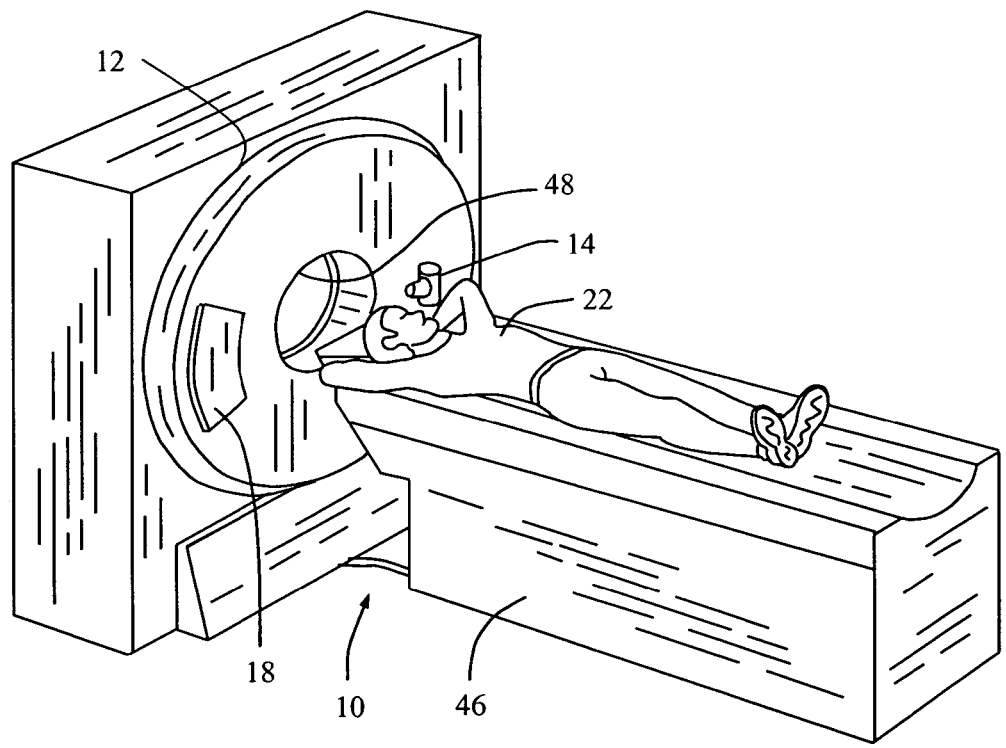
FIG. 1 is a pictorial view of a CT imaging system embodiment.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

To further improve the data acquisition, multi-slice or volumetric CT is built. Such a system collects multiple projections simultaneously by using a detector consisting of multiple detector rows. In such configuration, the fan beam geometry becomes a cone beam geometry.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
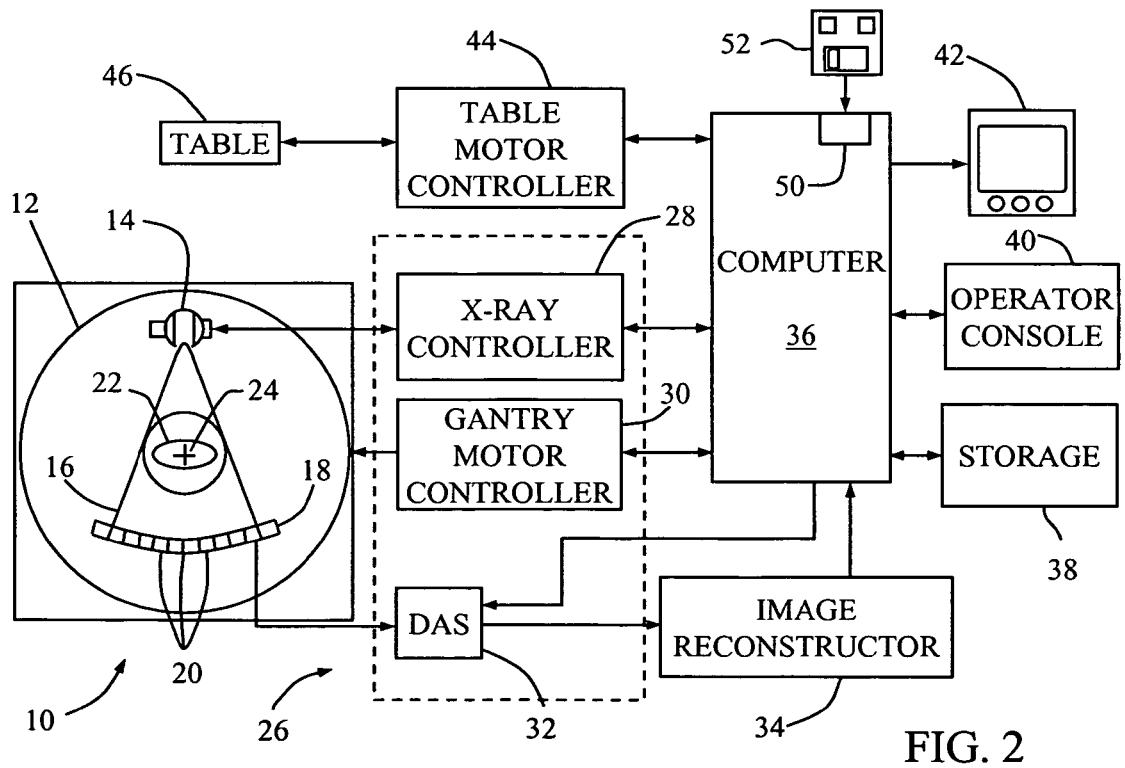
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the embodiments described herein are not limited to practice in CT system 10 and can be utilized in connection with many other types and variations of imaging systems. In one embodiment, computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, field programmable gate arrays (FPGA) and all other programmable circuits.

Herein described are new methods, apparatus, and software for accurate geometric forward modeling of third generation CT scanners that is suitable for iterative reconstruction of high quality clinical images for medical diagnostic purposes. The herein described methods support all configurations of CT scanners, including single-slice and multi-slice CT, as well as any trajectory of acquisition, such as step-and-shoot (axial) mode, helical mode, or any other mode, with constant or varying pitch and sampling patterns. The herein described methods are also applicable to fourth and fifth generation scanners such as a electron beam CT scanner (EBCT) such as are commercially available from GE Imatron of South Sanally, images have been reconstructed from CT data using so-called direct reconstruction algorithms such as filtered back-projection (FBP) or convolution back-projection (CBP). New iterative reconstruction (IR) algorithms are being introduced for the reconstruction of CT images. One advantage of IR algorithms is that they can more accurately model the measurements obtained from real CT systems. This is particularly true for helical CT systems with multi-slice detectors because these systems produce projection measurements that pass obliquely through the 2-D reconstructed image planes. By more accurately modeling these projections, IR algorithms can produce reconstructions with higher quality, lower noise, and fewer artifacts.

Figure 3:
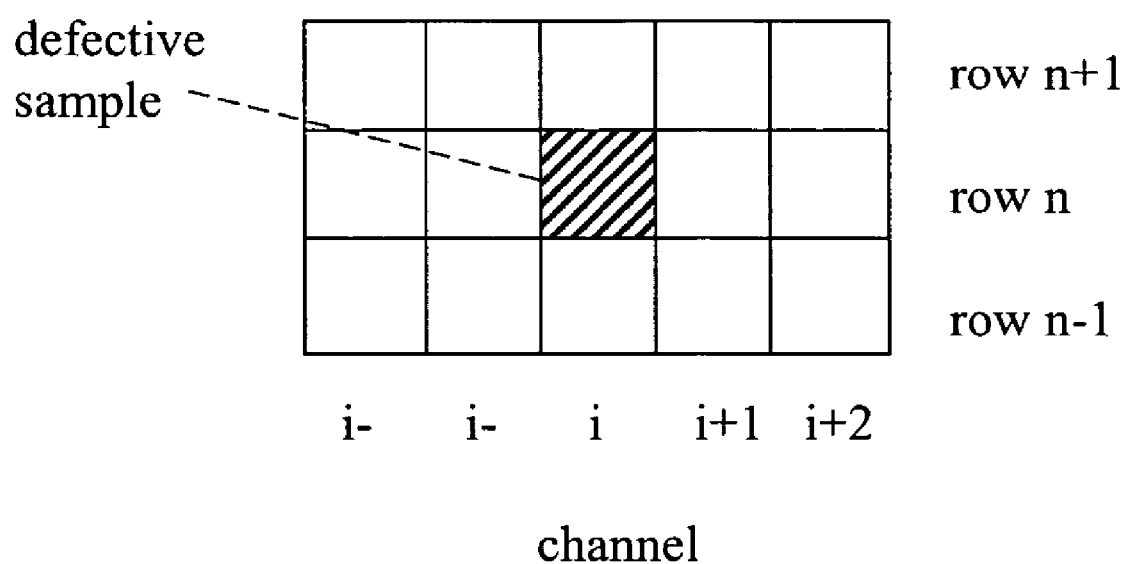
FIG. 3 illustrates an example of an at least partially unresponsive detector cell within a detector array.

For example, consider a helical scan CT system as depicted in FIG. 3. The 3-D volume to be reconstructed can be represented by an array of N discrete voxels $x_i$ where i is the index of the voxel's 3-D position. The value $x_i$ may specify the unknown density of the voxel. Furthermore, let $x=[x_1,x_2, \ldots ,x_N]$ be a vector containing the unknown density of each voxel in the reconstruction. So in this case, x represents the full 3-D reconstruction volume. During the CT scanning process, projections are measured for M different projections through the object. The different projections are typically measured for a wide variety of positions and angles through the object. The value of the integral mth projection through the object is denoted by $y_m$ and the vector of all measurements is denoted by $y=[y_1,y_2, \ldots ,y_M]$.

The objective of IR algorithms is to determine the unknown value of x by searching for the value of the vector x that best matches the measured data. Typically, this is done by minimizing a cost function of the form $$\hat{x} = \underset{x}{\operatorname{argmin}}\left\{\sum_{m=0}^{M} w_m |y_m - F_m(x)|^2\right\} \quad (1)$$

where $\hat{x}$ is the value of the variable x which achieves the minimum of the function, and wherein F is a transformation of the image space x and $w_m$ is a weight. This cost function can be minimized in a variety of manners using optimization methods such as iterative coordinate descent, expectation maximization, conjugate gradient, or any number of alternative techniques.

In practice, the solution to (1) is often too noisy. This noisiness may result when there are two few measurements, when the quality of the measurements is poor, or when the available projection angles and locations do not give sufficient information about x to properly reconstruct it. This problem can be addressed by adding an additional stabilizing function S(x) to the cost function being minimized. This results in the regularized inverse $$\hat{x} = \underset{x}{\operatorname{argmin}}\left\{\sum_{m=0}^{M} w_m |y_m - F_m(x)|^2 + S(x)\right\} \quad (2)$$

In one embodiment, the function S(x) is chosen to be a quadratic function with the form $S(x)=x^t H x$ where H is a symmetric and positive definite or positive semi-definite matrix. Additionally, in one embodiment, S(x) is a functional, and the particular choice of the functional can have a substantial effect on the quality of reconstructions produced by IR algorithms.

One method to minimize the impact of the failed or degraded detector channel and DAS channel is to derive an algorithm that can accurately estimate the missing projection samples based on the neighboring good samples. For the convenience of discussion, let the projection sample corresponding to detector row n and channel i be defective, as shown in FIG. 3. This can be the result of either detector failure or DAS failure. The projection sample for this channel is denoted by $p_k(i, n)$, where k is the view index. Note that here we have changed the indexing scheme from 1D to 3D. In the previous notation, the index for the measurement vector $y_m$ is not specifically arranged in terms of detector rows and detector channels. It is only arranged in terms of view index m. For the convenience of our current discussion, we provide additional indexes to the array (detector row n and channel i) so that existing defective detector correction can be discussed. Although different in their appearance, both notations specify the same measurement.

One way of estimating $p_k(i, n)$ is to perform a linear or bilinear interpolation using the neighboring signals. That is, $p_k(i, n)$ is estimated using the average signals of $p_k(i-1, n)$ and $p_k(i+1, n)$ for linear interpolation, and $p_k(i-1, n), p_k(i+1, n)$, $p_k(i, n-1)$, and $p_k(i, n+1)$ for bilinear interpolation embodiment has computational advantage with respect to speed, it may suffer from image artifacts. To overcome this potential shortcoming, one embodiment relies on interpolation in the Sinogram space. That is, the missing projection sample, $p_k(i, n)$, is estimated based on the samples of $p_{k-1}(i-1, n)$, $p_{k-1}(i, n), p_{k-1}(i+1, n), p_k(i-1n), p_{k+1}(i-1, n), p_{k+1}(i, n),$ and $p_{k+1}(i+1, n)$. Note that the estimation of a sample for view k requires not only the previously collected views, but also the next view, k+1. That is, one has to wait for the arrival of the future projection before the current projection can be corrected. In addition, although this approach further reduces image artifacts, residual artifacts may still remain. To overcome these potential shortcomings, a different approach follows. Instead of estimating the projection samples based on the adjacent views, one embodiment utilizes information from adjacent detector rows. It first performs higher order interpolation along index i for each of the three detector rows: n−1, n, and n+1. Since the signals $p_k(i, n-1)$ and $p_k(i, n+1)$ are measured from good detector cells, one can compare the interpolated signals for these two rows against the actual measurement. This step provides estimation of additional adjustments that may be needed for the interpolated signal on detector row n. The final estimated projection is then the interpolated signal plus the weighted sum of the additional adjustments from rows n−1 and n+1. This method has been shown to be quite effective in combating image artifacts. All of these methods, however, treat a detector either as a "perfect" channel or as a "bad" channel. In reality, however, many detector cells fall into the category in between. Below are described methods, systems, and software that overcome the above shortcomings.

For iterative reconstruction, the knowledge of the detector status can be integrated into the reconstruction process as a priori knowledge. To incorporate this information, and in accordance with one embodiment, one performs the following. For each detector sample, $p_k(i, n)$, a quality factor $q(i, n)$ is assigned. The $q(i, n)$ is obtained from the calibration process to indicate the "health status" of each detector cell. For example, if a detector cell performs within its specification, the corresponding $q(i, n)$ is assigned a value of 1. If a cell is completely non-functional (no valid signal is produced), $q(i, n)$ is assigned a value of 0. If the performance of the detector is somewhat degraded, $q(i, n)$ is assigned a value between 0 and 1, depending on its actual performance. For example, it is often discovered that detector performance can degrade over time. A detector can be degraded due to radiation damage, thermal characteristics change, or reflector reflectivity reduction. This behavior would not render the detector completely unusable. It merely makes the measured signal deviate from the true signal. The amount of deviation will be within a specified range. Therefore, the quality factor, $q(i, n)$, represents the degree of the measured data that can be trusted. The quality factor can be used, in one embodiment, as a multiplicative factor to the weighting matrix.

The cost function can be determined by the quality factor. For example, consider equation (2). The objective is to weight the error terms, $|y_m-F_m(x)|^2$, heavily for high quality detector samples, and weight the error terms lightly or zero for low quality detector samples. This can be done by assigning a weighting function, $\eta_m$, where the range of the function can be (0, infinity), based on the value of $q(i, n)$. (Please note the weighting function symbol is changed to differentiate from the weighting function in Eqs. 1 & 2). For example, if $q(i, n)=0$, the weighting $\eta_m$ can be very small or zero. In this case, the error term is negligible or discounted from the optimization function. On the other hand, if $q(i, n)=1$, $\eta_m$ may be large to heavily weight the high quality measurement. The weight $\eta_m$ may also vary based on other aspect of the data, such as noise property or geometry.

The minimization of the cost function now takes the form:

$$\hat{x} = \underset{x}{\operatorname{argmin}}\left\{\sum_{m=0}^{M} w_m|\eta_m[y_m - F_m(x)]|^2 + S(x)\right\} \quad (3)$$

In the above example, a quadratic error term may be replaced by a non-quadratic function with the form: $d[\eta_m(y_m-F_m(x))]$, where $d(\ )$ is a positive function that measures the error between $y_m$ and $F_m(x)$.

In some cases, iterative reconstruction algorithms may not directly minimize a cost function. For example, order-subset-expectation-maximization (OSEM) dynamically minimizes a varying cost function using a subset of the dataset. In this case, the cost function and data subset vary as a function of the iteration number. The method described above can also be applied in this case. But the weightings for each data term are used to modify the dynamically varying cost function at each iteration.

Another potential application of iterative reconstruction to the degraded components is to build the characteristics of the degraded components into the point-spread-function (PSF) model. For example, one can integrate the detector crosstalk into the PSF model. For example, certain photo diode types are known to produce electrical crosstalk in which a percentage of the signals from the neighboring cells is "bleeding" into the current cell. If not corrected, system spatial resolution is impacted. In the reconstruction process, the crosstalk can be modeled into the PSF model so that the spatial resolution can be recovered. It can also be incorporated into the weighting matrix.

Note that the use of the term PSF is in its broader sense. The first case represents a use of the term "point spread function" in the sinogram in the sense most often applied in the literature, while the second case uses the word "point" more broadly to represent a single voxel projected to a point on the sinogram. These two cases are treated separately.

These quality factors can be determined adaptively and updated during the reconstruction process. The quality factor for detector n can be determined by the nearby detectors. It can also be dependent on the images collected from other modalities or other a priori information.

One technical effect of the herein described methods, apparatus, and software is degradation of images due to failed or degraded components is reduced or eliminated.

While the invention has been described in terms of various specific embodiments, those skilled in the art will recognize that the invention can be practiced with modification within the spirit and scope of the claims.

What is claimed is:

1. A method for improving images of an imaging system including a plurality of detector cells, said method comprising:
   assigning a quality factor for each detector cell wherein the quality factor is determined during a calibration process to indicate the "health status" of at least one of the plurality of detector cells, the quality factor being assigned a first value when the cell is within specifications, the quality factor being assigned a second value different than the first value when the cell is unresponsive; and
   generating a weight function $\eta_m$ for a plurality of detector cells based on the quality factors of each particular detector cell.

2. A method in accordance with claim 1 further comprisingusing the weight function $\eta_m$ to weigh an error term.

3. A method in accordance with claim 2 further comprising using the weight function $\eta_m$ to generate a cost function used for the modification of a reconstructed image.

4. A method in accordance with claim 3 further comprising using the weigh function $\eta_m$ to generate a cost function used for the modification of the reconstructed image, wherein the cost function is minimized (or maximized) through at lease one pass through the data corresponding to the plurality of the detector cells.

5. A method in accordance with claim 2 further comprising using the iterative reconstruction techniques to produce an image.

6. A method in accordance with claim 1, wherein said assigning a quality factor for each detector cell comprises:
   assigning to each detector cell a quality factor value and the second value when the cell is not within the specifications and is partially responsive.

7. A method in accordance with claim 6 further comprising generating a weight function $\eta_m$ for a particular detector cell based on the quality factor of that particular cell.

8. A method in accordance with claim 1, wherein said assigning a quality factor for each detector cell comprises:
   assigning a logical "1" to the quality factor for each detector cell when the cell is within a predetermined specification; and
   assigning a logical "0" to the quality factor for each detector cell when the cell is outside the predetermined specification.

9. An imaging system comprising:
   a radiation source;
   a detector array comprising a plurality of cells positioned to receive radiation from said source; and
   a computer coupled to said detector array; said computer configured to:
   obtain from a memory a quality factor for each detector cell wherein the quality factor is determined during a calibration process to indicate the "health status" of at least one of the plurality of the detector cells, the quality factor being assigned a first value when the cell is within specifications, the quality factor being assigned a second value different than the first value when the cell is unresponsive;
   generating a weight function $\eta_m$ for a plurality detector cells based on the quality factors of each particular detector cell; and
   use the quality factors to reconstruct an image.

10. An imaging system in accordance with claim 9, wherein said computer further configured to reconstruct an image using a weight function $\eta_m$ for a particular detector cell wherein the weight function $\eta_m$ is based on the quality factor of that particular detector cell.

11. An imaging system in accordance with claim 10, wherein said computer further configured to use the weight function $\eta_m$ to weigh an error term.

12. An imaging system in accordance with claim 10, wherein said computer further configured to use the weight function $\eta_m$ to generate a cost function used for the modification of a reconstructed image.

13. An imaging system in accordance with claim 12, wherein said computer further configured to use the weight function $\eta_m$ to generate a cost function used for the modification of the reconstructed image, wherein the cost function is minimized (or maximized) through at least one pass through the data corresponding to the plurality of detector cells.

14. An imaging system in accordance with claim 9, wherein said computer further configured to use iterative reconstruction techniques to produce an image.

15. An imaging system in accordance with claim 9, wherein said radiation source comprises an x-ray source, and said computer configured to perform computed tomography (CT).

16. A computer readable medium encoded with a program configured to instruct a computer to assign a quality factor for each of a plurality of detector cells wherein the quality factor is determined during a calibration process to indicate the "health status" of at least one of the plurality of detector cells, the quality factor being assigned a first value when the cell is within specifications, the quality factor being assigned a second value different than the first value when the cell is unresponsive; and
   generating a weight function $\eta_m$ for a plurality of detector cells based on the quality of each particular detector cell.

17. A computer readable medium in accordance with claim 16, wherein said program further configured to instruct the computer to generate a weight function $\eta_m$ for a particular detector cell based on the quality factor of that particular detector cell.

18. A computer readable medium in accordance with claim 16, wherein said program further configured to instruct the computer to:
   assign to each detector cell a quality factor value between the first value and the second value when the cell is not within specifications and is partially responsive.

19. A computer readable medium in accordance with claim 18, wherein said program further configured to instruct the computer to generate a weight function $\eta_m$ for a particular detector cell based on the quality factor of that particular detector cell.

20. A computer readable medium in accordance with claim 19, wherein said program further configured to instruct the computer to using the weight function $\eta_m$ to weigh an error term.

* * * * *